United States Patent [19]

Beigler et al.

[11] 4,029,773

[45] June 14, 1977

[54] COMPOSITION AND METHOD OF TREATING ULCERS

[75] Inventors: Myron A. Beigler, Palo Alto; Ronald J. Amen, Villa Park, both of Calif.

[73] Assignee: Syntex (U.S.A.) Inc., Palo Alto, Calif.

[22] Filed: May 25, 1973

[21] Appl. No.: 364,144

[52] U.S. Cl. .............................. 424/180; 424/274; 424/312; 424/319

[51] Int. Cl.$^2$ ....................................... A61K 31/70

[58] Field of Search ........... 424/180, 319, 145, 312

[56] References Cited

UNITED STATES PATENTS

| 3,697,287 | 10/1972 | Winitz | 424/319 |
|---|---|---|---|
| 3,773,930 | 11/1973 | Mohammed et al. | 424/319 |

OTHER PUBLICATIONS

*Handbook of Therapy*, 11th Ed., (1937), pp. 372–375.
*The Extra Pharmacopoeia*, vol. 1, (1952), pp. 1032–1033.

*Primary Examiner*—Frederick E. Waddell
*Attorney, Agent, or Firm*—Lawrence S. Squires; William B. Walker

[57] ABSTRACT

Compositions and method for treating, or reducing the occurrence, of stomach and duodenum ulcers. The compositions and methods are characterized by the administration of a composition containing (dry weight basis) 10 to 40% sucrose; 10 to 40% glucose; 12 to 20% amino acids and 7.5 to 12% lipids. The composition is typically administered orally as an aqueous liquid emulsion.

22 Claims, No Drawings

COMPOSITION AND METHOD OF TREATING ULCERS

BACKGROUND OF THE INVENTION

1. The Invention

This invention relates to compositions and methods for treating ulcers occurring in the stomach and/or the duodenum of humans. In a further aspect this invention relates to prophylactic compositions and methods for preventing or reducing the frequency of ulcers in the stomach and/or the duodenum. In a still further aspect this invention relates to compositions comprising sucrose, glucose, amino acid mixture having the essential amino acid pattern of naturally occurring proteins and lipids. In another aspect this invention relates to methods and compositions for treating gastric intestinal ulcers or preventing or reducing the frequency of gastric intestinal ulcers occurring in mammals.

2. The Prior Art

Stomach and intestinal ulcers, and particularly peptic ulcers, are one of the most disturbing and incapacitating painful disorders occurring in man and if not properly treated, can be fatal in both man and lesser animals. Peptic ulcers have been defined as "a circumscribed erosion of the mucous membrane penetrating through the muscularis mucosa, involving the mucosal areas exposed to acid-pepsin secretion" and typically occur on the lesser curvature of the stomach or in the first section of the duodenum. The individual ulcers have clearly defined borders within the mucosa and resemble craters having a smooth crater floor comprising a thin layer of exudate covering a deeper layer of granular or fibrous tissue. At the present time, peptic ulcers are generally treated by prescribing relatively complete bed rest for periods of one to three weeks and complementary medication designed to minimize hyperacidity and intestinal spasm (e.g. reduce anxiety and nervous tension). In severe cases where the patient does not respond to this treatment, surgery is generally required. A number of special diets have been proposed for treating ulcers, however, with the exception that there is general agreement that highly seasoned or greasy foods and roughage are detrimental, there is much controversy as to whether such diets are effective. It is further known that the pain pattern of duodenal ulcers typically occurs two to three hours after meals and can be relieved by certain bland food and/or antacids. Accordingly, we have invented novel nutritional compositions containing certain nutrients in combination with a relatively high ratio of lipid and sucrose which provide exceptionally long gastric retention periods thus prolonging the period of freedom from pain in patients suffering from duodenal ulcers. We have further surprisingly, and more importantly, discovered that based on small animal laboratory tests that our nutritional composition is able to greatly increase both the rate of healing and success frequency of healing both duodenal ulcers and stomach ulcers.

SUMMARY OF THE INVENTION

The compositions of the invention have both a dry form and a wet form. The dry form of our composition is primarily used for storage whereas the liquid form is used for actual administration. In summary, the dry form of our composition comprises, based on weight percent, 10 to 40% sucrose; 10 to 40% glucose; 12 to 20% amino acid mixture containing all of the essential amino acids in the same amino acid patterns as found in naturally occurring protein and optionally containing one or more non-essential amino acids; and 7.5 to 12% lipids having a high ratio of polyunsaturated lipids to saturated lipids.

In summary, the liquid form of the composition in the invention comprises the dry composition, of the invention, in mixture, preferably as an emulsion, with water, or other pharmaceutical compatible liquid, in a ratio such that 1 ml. of the liquid mixture has an energy content of about 0.5 through 2 kilo-calorie and has an osmolality of about from 400 to 1500 milliosmols per kilogram.

In summary, the process, of the invention, for treating ulcers comprises orally administering to human patients suffering from stomach and/or duodenal ulcers, about from 12 to 20 oz. (360 to 600 gm.) of the liquid composition, of the invention, per day, preferably at 3 to 5 servings of 4 oz. per serving. In summary, the process of our invention for prophylactically administering the liquid composition to human patients comprises orally administering about from 240 to 600 g. per day of the liquid composition, of our invention, to patients who have a high susceptibility to stomach and/or duodenal ulcers.

The compositions and processes of the invention will be further described herein below.

FURTHER DESCRIPTION OF THE INVENTION AND PREFERRED EMBODIMENTS

Considering the composition, of the invention, in greater detail, the dry formula of the composition comprises, based on weight percent, from 10 to 40% and preferably 25 to 35% sucrose; 10 to 40% and preferably 25 to 35% glucose; 12 to 20%, and preferably 15 to 20%, amino acid mixture containing all of the essential amino acids in the same amino acid patterns as found in naturally occurring protein and optionally containing one or more non-essential amino acids; and 7.5 to 12%, preferably 9 to 11%, pharmaceutically acceptable lipids having a high ratio of unsaturated lipids to saturated lipids; and wherein at least 50% of the composition is composed of said sucrose, glucose, lipid and amino acid. The remaining portion of the composition can be any pharmaceutically acceptable material such as, for example, conventionally used in the art. A convenient pharmaceutically acceptable filler material which can be used in our composition is corn starch. The composition, further has an aqueous emulsion osmolality of about from 400 to 1500 milliosmols per kilogram at a concentration of about from 0.1 to 0.5 g/ml. Best results are typically obtained by using a composition having each of the above listed components in the preferred range. Further, it is desirable that the composition also contain a pharmaceutically acceptable emulsifying agent to facilitate dispersion of the dry composition within a liquid medium (e.g. water). Suitable emulsifying agents which can be used include, for example, carrageenans, starches, food-grade gums of polysaccharide structure, mono- and diglyceride, lecithin, and other emulsifying agents known in the art to encourage emulsion formation. Also, where an emulsifying agent is used, only a small amount is required, typically less than 1%, by wt., however, the optimum quantity will, of course, vary with the particular emulsifying agent used. The term lipids, as used herein, refers to the constituents of protoplasm which are essentially insoluble in water but are alcoholether soluble. Lipids [as defined by Deuel, H. J., Jr., *The Lipids: Their Chemistry and Biochemistry*, Chemistry, Vol. 1, Interscience Publishers, New York (1951)] include fats, fatty acids, fatty oils, essential oils, waxes, sterols, phospholipids, glycolipids, sulfolipids, aminolipids, chromolipids and the like. Typically, the lipids used in our compositions are free fatty acids and/or triglycerides of fatty acids containing a relatively high ratio of polyunsaturated fatty acids and/or triglycerides of polyunsaturated fatty acids to saturated fatty acids and/or triglycerides of saturated fatty acid. By a relatively high unsaturated to saturated ratio is meant a molecular ratio in excess of 1:1. The lipids occur in the proper ratio, for use in our composition, in many naturally occurring substances and thus such substances or mixtures thereof can be used directly in our composition. Suitable naturally occurring substances include, for example, soybean oil, corn oil, safflower oil, peanut oil, cotton seed oil, and the like, and mixtures thereof.

As used herein above and below, the prefix term pharmaceutically acceptable or pharmaceutically compatible refers to agents or substances which do not meaningfully adversely affect the pharmaceutical properties (e.g. toxicity, effectiveness, etc.) of the composition.

The amino acid mixture used in our compositions contains all of the essential amino acids, and optionally can contain one or more non-essential amino acids, and further contains the essential amino acids in the same relative ratio to each other as they are found in corresponding natural proteins (e.g. egg albumin, milk casein, etc.). Thus, the amino acid mixture used in the composition can be easily prepared in the proper ratio by hydrolyzing a readily available natural protein such as, for example, egg albumin and then optionally adding one or more essential or non-essential amino acids. Further, while we have found that good results are obtained with any amino acid pattern found in naturally occurring proteins containing all the essential amino acids, we have further found that exceptionally good results are obtained by using the amino acid pattern of egg albumin. Typically, a number of these amino acids occur as, or are commercially supplied as, salts and accordingly the term amino acid mixture also encompasses pharmaceutically acceptable salts of the above defined amino acids.

Thus, the amino acids used in the composition include all of the amino acid art recognized as and designated as "essential amino acids" and optionally can include one or more amino acid arts designated as "non-essential amino acids". The essential amino acids are leucine, isoleucine, valine, methionine, tryptophan, phenylalanine, threonine, arginine, lysine, and histidine and includes pharmaceutically acceptable salts thereof. The term non-essential nutritional amino acids refer to amino acids providing a source of metabolizable nitrogen, which is required by the animal organism for biosynthesis of proteins, nucleic acids, etc. Suitable non-essential amino acids include, for example, alanine, cysteine, cystine, glycine, proline, glutamic acid, tyrosine, hydroxyproline, aspartic acid, serine and the like and pharmaceutically acceptable salts thereof.

Further, since the osmolality of the liquid form of the composition should be in the range of about from 400 to 1500, and preferably 400 to 800 milliosmols per kg., and further as the osmolality is primarily controlled as a function of the molecular weights of the particular monomers used and quantities thereof, the osmolality of the liquid composition can be conveniently and easily adjusted within this range by selection of the monomers and quantities used.

Optionally, the composition, of the invention, can also contain small quantities of pharmaceutically compatible minerals, healing agents (e.g. zinc salts such as, for example, zinc sulfate), medicaments, vitamins, antacids or buffering agents (e.g. sodium acetate) preferably in very small quantities (i.e. less than 1%, by wt.) for any given additive and in the case of healing agent and medicaments, preferably less than 0.01%. Also, where palatability is a factor, small quantities of conventional pharmaceutically acceptable flavoring agents can be added, e.g. flavor esters, alcohols, aldehydes, terpines, sesquiterpines, hydrocarbons and the like. For instance, these constituents can be made into or be contained in conventional flavors such as imitation or natural vanilla, chocolate or the like.

The dry form of our composition can be prepared according to any suitable mixing or compound procedures, for example, the composition can be conveniently prepared by dry blending all ingredients in any suitable powder blender. For efficient results, a liquid-solid blender with fat injection apparatus can be used.

The liquid form of our composition essentially consists of a mixture, preferably an emulsion, of the dry form of our composition in water or other pharmaceutically compatible liquid. The ratio of dry composition and water (or other liquid) is adjusted such that 1 ml. of the liquid mixture has an energy content of about from 0.5 to 2 kilo-calories. Typically, the calorie content of the dry composition can be readily calculated since the primary components of the composition are known materials for which caloric contents have already been determined or, alternatively, the caloric content or the composition can be determined according to standard calometric procedures. Typically, the dry composition has an energy content of about 4 or 5 kcal, per gram, and thus the liquid mixture will typically contain about from 0.1 to 0.5 g. of the dry composition per milliliter.

The nutritional compositions, of the invention, are administered orally in their liquid form, preferably as liquid emulsions; typically aqueous emulsions. Also where an emulsifying agent has not been used, the composition should be shaken immediately prior to administration to disperse the insoluble particules throughout the liquid medium. The nutritional composition can be fed to the patient in place of the patient's normal nutrient intake or as a part of, or in supplement to the patient's normal nutrient intake. Accordingly, the quantity of dosage of composition administered can vary over wide ranges depending upon the particular patient and the severity of the ulcer condition. Thus, where the composition is being administered prophylactically or to treat relatively mild ulcer conditions, relatively smaller dosages need be administered. Typically, when the composition is administered prophylactically, adult dosages in the range of about from 10 to 200 g. (dry basis) per day are used. Conversely where the patient has a severe ulcer condition, or where the patient's entire nutritional intake is supplied by the composition, larger quantities of the composition are administered daily, subject to any limitations on the total intake of nutrients necessitated by the overall condition of the patient. Typically, where the composition is used to treat (heal) ulcers, the composition is administered daily in adult dosages in the range of about from 60 to 300 g. (dry basis) per day. Where the patient's entire nutrient intake is to be supplied by our composition, it should contain the proper balance of amino acids and such additional nutritional supplements, e.g. vitamins, as required by the patient.

Recently it has been recognized that gastric-intestinal ulcers also pose a serious problem in non-primate mammals; notably pigs and cattle. Accordingly, our composition — not surprisingly because of the similarity of the gastric-intestinal tracts of humans and pigs — can also be used to treat ulcers in such mammals and especially pigs. In such cases the dosage range will vary over a wide range depending upon the severity of the ulcer condition and the condition of the host and further in the case of food animals, the economics of the situation. Typically, however, the dosage will fall within the range of about 0.5 to 5.0 grams per kilogram on a dry basis per day.

The exact mechanism of healing effected by our composition is not clearly understood, however, it is conjectured that the exceptional increase in gastric residence time produced by the sucrose and lipid components of our composition allows the nutrient components (i.e. glucose and amino acids) to bathe the ulcer and remain in contact with the cells of the mucosa surrounding the ulcer for an unusually long period of time. Since glucose and amino acids are monomer forms of nutrients, they are capable of being directly assimilated by the cell. This large increase in residence time permits or induces direct feeding of the mucosal cells from the lumen side (ulcer side) in contrast to normal systemic feeding which occurs from the serosal side of the gastric/duodenal wall. This direct feeding of the mucosal cells surrounding the ulcers thus promotes or facilitates rapid and efficient healing of the ulcer lesion or erosion.

A further understanding of the invention can be had from the following non-limiting Examples.

EXAMPLE 1

This example illustrates the action of our composition versus a standard nutrition diet and a negative control (complete fasting). In this example 35 male Sprague-Dawley rats, weighing about 170 grams each, were depilated and then subjected to 65% whole body burn (a procedure which is known to induce stress ulcers in such rats; see Langlois, P. L., Williams, H. B., and F. N. Guid, 1972, Effect of an Elemental Diet on Mortality Rates and Gastrointestinal Lesions in Experimental Burns, the Journal of Trauma, 12:771–777). The rats were then placed into separate cages and divided into Groups A, B, and C containing 15 rats; 10 rats; and 10 rats, respectively. Group A was fed a test diet composition, according to our invention, as an emulsified liquid (aqueous emulsion containing 25%, by wt., solids and supplying about 1 kcal/ml.). Group B was fed typical commercial chow (i.e. Purina Lab Chow Trademark, sold by Ralston Purina Company of St. Louis, Missouri, as a control diet and Group C was fasted as a negative control. The animals in all groups were given water ad libitum. After 48 hours, all the rats were sacrificed and the stomachs and proximal intestines removed and immediately placed in buffered formalin to ensure preservation. The stomachs and intestines were examined grossly for any obvious morphological changes and then five sections from each stomach and four sections from each intestine were examined microscopically. The results are summarized in the following table:

TABLE I

| Test Diet*[1] (15 rats) | Control Diet*[2] (10 rats) | Negative Control (10 rats) |
| --- | --- | --- |
| Stomach "normal" slight autolysis within the limits of histological variation | Stomach 5 rats showed slight vesicular congestion including focal congestion of the villi, ulceration and mucosal edemations | Stomach all 10 rats had pathology and microscopic changes in the mucosa |
|  | 1 severe ulcer | 6 rats focal congestion of the tips of the villi |
|  | 1 erosion | 6 rats had erosion of the mucosal epithelium primarily at the tips of the villi |
| Duodenum "normal" | Duodenum 6 rats had swollen villiedema, irritation/inflammation and stroma of villi edemation, however, the epithelium lining of the villi was normal | Duodenum 2 rats had erosion |
|  |  | 5 rats had gross morphological changes. Severe erosions of mucosal epithelium, inflammation, focal congestion |

*[1]The composition of the Test Diet (dry weight basis) was as follows:

| | |
| --- | --- |
| sucrose | 34.5% |
| glucose | 34.5% |
| amino acid mix** | 17.67% |
| soybean oil | 10.00% |
| U.S.P. mineral diet mix XVII | 2.50% |
| AOAC vitamin mix | 1.00% |
| sodium acetate | 0.11% |
| $ZnSO_4 \cdot H_2O$ | 0.0015% |

**The amino acid mix used in the Test Diet had the following composition:

AMINO ACID MIX***

| Amino Acid | Percent (wt.) |
| --- | --- |
| l-glutamine | 16.23 |
| glycine | 12.01 |
| l-lysine HCl | 9.96 |
| l-arginine HCl | 7.64 |
| l-phenylalanine | 6.45 |
| l-leucine | 6.11 |
| Na-l-aspartate | 5.87 |
| l-serine | 5.00 |
| l-methionine | 4.53 |
| l-isoleucine | 4.53 |
| l-threonine | 4.53 |
| l-valine | 4.53 |
| l-histidine | 3.06 |
| l-alanine | 1.92 |
| l-proline | 1.92 |
| l-cystine | 1.92 |
| l-tyrosine | 1.92 |
| l-tryptophan | 0.96 |

***Corresponds to the essential amino acid pattern of egg albumin, plus non-essential amino acids.
*[2]The composition of the Control Diet was composed of meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacine, vitamin A supplement, D activated plant sterol, vitamin E supplement, calcium carbonate, dicalcium phosphate, iodized salt, iron sulfate, iron oxide, manganous oxide, cobalt carbonate, copper oxide, zinc oxide, and had a guaranteed analysis of:

| | |
| --- | --- |
| Crude protein not less than | 23.0% |
| Crude fat not less than | 4.5% |
| Crude fiber not more than | 6.0% |
| Ash not more than | 9.0% |

Obviously many modifications and variations of the invention, described herein above and below in the Claims, can be made without departing from the essence and scope thereof.

What is claimed is:

1. A composition, useful in the treatment and prevention of gastric intestinal ulcers, comprising from 10 to 40% wt. sucrose; 10 to 40% wt. glucose; 12 to 20% wt. amino acid mixture containing at least all of the essential amino acids, or pharmaceutically acceptable salts thereof, in the same relative ratio to each other as the essential amino acids are found in naturally occurring proteins; and 7.5 to 12% wt. lipid selected from the group consisting of soybean oil, corn oil, safflower oil, peanut oil, cotton seed oil, and a mixture thereof; said composition having an aqueous emulsion osmolality of about from 400 to 1500 milliosmols per kg., at a concentration of 0.1 to 0.5 g. of said composition per ml. wherein at least 50% of said composition is composed of said sucrose, glucose, amino acid mixture and lipid.

2. The composition of claim 1 wherein said composition also comprises a pharmaceutically acceptable emulsifying agent in an amount of less than 1% by wt.

3. The composition of claim 2 wherein said emulsifying agent is selected from the group consisting of carrageenans, starches, food-grade gums of polysaccharide structure, monoglycerides, diglycerides, lecithin and mixtures thereof.

4. The composition of claim 1 wherein said amino acid mixture includes at least one non-essential amino acid or pharmaceutically acceptable salt thereof.

5. The composition of claim 1 wherein said amino acid mixture has the same essential amino acid pattern as egg albumin.

6. The composition of claim 1 wherein said composition comprises from 25 to 35% wt. sucrose; 25 to 35% wt. glucose; 15 to 20% wt. of said amino acid mixture and 9 to 11% said lipid.

7. The composition of claim 4 wherein said composition contains about 34.5% wt. sucrose; 34.5% wt. glucose; 10% wt. soybean oil; and about 17.7% of said amino acid mixture and wherein said essential amino acid has the pattern of egg albumin and wherein said non-essential amino acid is selected from the group consisting of 1-glutamine; glycine; sodium-1-aspartate; 1-serine; 1-alanine; 1-proline; 1-cystine; 1-tyrosine and mixtures thereof.

8. A liquid composition, useful in the treatment and prevention of gastric intestinal ulcers, having an osmolality of about from 400 to 1500 milliosmols per kg. consisting essentially of the composition of claim 1 in mixture with a pharmaceutically acceptable liquid medium in a ratio such that 1 ml. of said composition has an energy of about from 0.5 through 2 kilocal.

9. The liquid composition of claim 8 wherein said amino acid mixture includes at least one non-essential amino acid or pharmaceutically acceptable salt thereof.

10. The liquid composition of claim 8 wherein said amino acid mixture has the same essential amino acid pattern as egg albumin.

11. The liquid composition of claim 8 wherein said composition contains a pharmaceutically acceptable emulsifying agent, in an amount of less than 1% on a dry wt. basis.

12. The liquid composition of claim 11 wherein said emulsifying agent is selected from the group consisting of carrageenans, starches, food-grade gums of polysaccharide structure, mono- and diglycerides, lecithin and mixtures thereof.

13. The composition of claim 8 wherein said liquid medium is water.

14. A liquid composition, useful in the treatment and prevention of gastric intestinal ulcers, having an osmolality of about from 400 to 1500 milliosmols per kg. consisting essentially of the composition of claim 7 in mixture with a pharmaceutically acceptable liquid medium in a ratio such that 1 ml. of said composition has an energy content of about from 0.5 through 2 kilcal.

15. A method for healing ulcers occurring in the stomach or duodenum of mammals which comprises orally administering to mammals having stomach ulcers or duodenal ulcer an effective amount of the composition of claim 8.

16. The method of claim 15 wherein said composition is administered to human beings in a dosage range of about from 60 to 300 grams of said composition on a dry wt. basis per day.

17. The method of claim 15 wherein said composition is administered in a dosage range of about from 10 to 300 grams dry wt. basis per day.

18. The method of claim 15 wherein said composition is administered to pigs.

19. A method of reducing the occurrance of stomach ulcers and duodenal ulcers in mammals which comprises orally administering a prophylactically effective amount of the composition of claim 8 to mammals which have a susceptibility to stomach ulcers or duodenal ulcers.

20. The method of claim 19 wherein said composition is administered to human beings in a dosage of about from 10 to 200 grams of said composition dry wt. basis.

21. The method of claim 19 wherein said composition is administered in a dosage range of about from 10 to 300 grams dry wt. basis per day.

22. The method of claim 19 wherein said composition is administered to pigs.

* * * * *